US005222950A

United States Patent [19]

Eisenberg

[11] Patent Number: 5,222,950

[45] Date of Patent: Jun. 29, 1993

[54] QUICK RELEASE TAMPER EVIDENT CLOSURE DEVICE

[76] Inventor: Melvin I. Eisenberg, 3849 Swanson Ct., Gurnee, Ill. 60031

[21] Appl. No.: 552,940

[22] Filed: Jul. 16, 1990

[51] Int. Cl.[5] ............ A61M 5/005

[52] U.S. Cl. ............ 604/408; 604/415; 215/249; 215/253; 215/256

[58] Field of Search ............ 604/403, 408-416; 215/200, 207, 250, 253-256, DIG. 3, 305

[56] References Cited

U.S. PATENT DOCUMENTS

| | | | |
|---|---|---|---|
| 3,788,374 | 1/1974 | Saijo | 604/408 |
| 3,902,477 | 9/1975 | Gerarde | 604/403 |
| 3,991,758 | 11/1976 | Mohrke et al. | 604/403 |
| 4,234,026 | 11/1980 | Bayham | 604/408 X |
| 4,303,067 | 12/1981 | Connolly et al. | 604/408 |
| 4,430,077 | 2/1984 | Mittleman et al. | 604/1 M |
| 4,553,970 | 11/1985 | Lewis, Jr. | 604/408 |
| 4,573,980 | 3/1986 | Karrasch et al. | 604/256 |
| 4,592,092 | 5/1986 | McPhee | 215/DIG. 3 |
| 4,632,267 | 12/1986 | Fowles et al. | 215/253 |
| 4,834,743 | 5/1989 | Valerio | 604/403 |
| 4,872,563 | 10/1989 | Warder et al. | 604/403 |
| 4,903,855 | 2/1990 | Ducay et al. | 215/253 X |
| 5,038,794 | 8/1991 | Van Vakenburg | 604/403 |
| 5,100,011 | 3/1992 | Maietta | 215/256 |

*Primary Examiner*—Robert A. Hafer
*Assistant Examiner*—Kerry Owens
*Attorney, Agent, or Firm*—Jerome Goldberg

[57] ABSTRACT

A quick release tamper evident closure device for disposable fluid medical storage bags. The closure device comprises an outlet port section and a closure cap section sealed together. The outlet port section is sealed to the bag and includes a tubular member for discharging the fluid in the bag. The outer end of the tubular memeber extends inside a cavity formed in the cap section. A tear path is formed around the cap section for severing the cap section from the port section to provide access to the tubular member. The tear path includes opposed curved portions merging into an apex. A handle extends outward from the cap section and aligned with the apex for applying an outward force which is initially concentrated at the apex, to cause ripping of the closure cap at the apex and then along the remainder of the tear path. The handle includes an opening and is flexible for varying the dimensions of the opening to accommodate the various sized finger inserted therethrough. The tear path may also include a second apex opposed to the first apex and the handle is aligned with both apexes. The applied force would be initally focused at the apexes.

28 Claims, 2 Drawing Sheets

QUICK RELEASE TAMPER EVIDENT CLOSURE DEVICE

BACKGROUND OF THE INVENTION

This invention relates generally to a quick release closure device for a disposable bag used for storing blood, a saline solution and other fluids necessary for the patient; and more particularly relates to a quick release closure device which is tamper evident and readily opened for accessing the fluid outlet of the bag.

A prior closure device for fluid disposable bags comprised an outlet port for discharging fluid and a closure cap sealed to the outlet port. A circular groove was formed inward on the outside of the cap section to provide a circular tear line for severing the cap from the outlet port, to afford access to the outlet port and the fluid contents in the bag. The cap section included an elongated handle for gripping and pulling outward to break open the circular tear line.

Often times the previous closure devices were difficult to open. The tear line did not readily rip apart. When blood or other life supporting fluids are urgently needed, particularly during surgery, any time delay due to the opening of the fluid bag could be detrimental to the life and well being of the patient.

The subject invention overcomes the problem heretofore experienced in the opening of closure devices for the fluid bags, by forming a tear path having opposed curved portions merging into an apex. The applied force is initially concentrated at the apex to immediately start the ripping of the tear path at the apex and then along the remainder of the tear path, to provide access to the outlet port.

Upon opening the closure device of a fluid disposable bag, a conventional IV set with a spike to pierce open the outlet port is usually attached to the outlet port of the fluid bag, and the bag is positioned on a hook located above the patient. In an operating room environment, after the closure device has been opened, the nurse or medical attendant had only one hand free to make attachments since the other hand was occupied holding the handle portion of opened closure cap. The nurse or medical attendant was then required to search for a disposal for depositing the handle. Sometimes the throw away handle would end up on the operating room floor, creating a hazard and the possibility of someone slipping and falling.

The subject invention overcomes the afore-described problem and provides a flexible handle for a closure device which includes a channel opening for receiving the finger of the nurse or medical attendant. After the closure device is opened the throw away handle may remain snugly supported on the finger until disposed of at a convenient time, thereby having both hands free to make necessary attachments or provide other assistance.

SUMMARY OF THE INVENTION

The quick release tamper evident closure device of the invention is sealed to the bottom end of a fluid disposable bag. The closure device comprises an outlet port section sealed to a closure cap section. The port section includes a tubular member for discharging fluid after being pierced open with a spike or the like. Any tampering with the closure device of the fluid bag would be immediately apparent prior to opening the closure device for use of the contents in the bag.

The closure cap section includes a neck portion having a cavity formed therein to receive the outer end of the tubular member. A groove circumscribes the outside of the neck to define a tear path. The tear path include curved or arcuate portions which merge together to form an apex. A handle extends outward from the neck and aligned with the apex. An outward force is applied to the handle which is initially focused at the apex to cause ripping of the closure cap at the apex and then along the remainder of the tear path. This opens the closure device and affords access to the tubular member of the outlet port section for attaching an "IV" set or other attachments.

The handle is flexible. An opening is formed in the handle which self adjusts to the size of the finger inserted therethrough for applying the tearing force.

The arcuate portions of the grooved tear path are opposed to each other and the apex is a projection angularly extending outward from the arcuate portions.

A depression is formed on the inside of the neck portion in communication with the neck cavity and having an apex or triangular configuration. The apex shaped depression forms the hollow inside for the apex projection on the outside of the neck.

A second protruding apex is positioned in the tear path spaced from and opposed to the other apex. Thus, The grooved tear path includes a pair of opposed arcuate portions merging together at opposite ends to form the opposed apexes protruding outward from the arcuate portions. A second depression also having an apex or triangular configuration is formed on the inside of the neck portion in communication with the neck cavity to form the hollow inside for the second protruding apex. The handle may have a substantially "U" shaped configuration enclosing the handle opening. The handle is positioned to align with both apexes.

When pulling outward on the handle with the finger inside the opening, the tearing force is immediately concentrated at the apexes and the ripping action spreads along the arcuate portions of the tear path until the cap is severed from the outlet port section to enable removal of the bag contents.

Therefore, a primary object of the invention is to provide a quick release tamper evident closure device for medical fluid disposable bags.

Another object is to provide a quick release closure device for a fluid disposable bag that is tamper evident.

Another object is to provide a quick release closure device that upon opening does not require the immediate disposal of the throw away portion of the closure device.

A primary feature of the quick release tamper evident closure device is to provide a curved tear path for opening the closure and including an apex for concentrating the initial applied force.

Another primary feature is to provide a handle for opening the closure and positioned substantially perpendicular to the tear path and aligned with the apex of the tear path.

Still another primary feature is to provide a flexible handle having an opening formed therein for receiving the finger of the nurse or medical attendant opening the closure. A related object is to provide an opening in the handle that self accommodates various sized fingers.

Another feature is to provide a curved tear path which includes a pair of apexes spaced apart and positioned opposed to each other in the tear path.

Still another feature is to provide a handle for the closure device which is aligned with the pair of apexes included in the tear path.

Another feature is to provide a circumscribing tear path including apexes which protrude outward with respect to the remaining portions of the tear path.

Another feature is to provide a circumscribing tear path having substantially the same wall thickness throughout eventhough the tear path includes one or more projections.

Yet another feature is to provide a closure cap section having a cavity therein and forming a depression inside the defining wall of the cavity to define an apex configuration within the curved tear path provided for opening the closure device.

Another feature is to provide the apex shaped depression on the inside of a wall portion to form the hollow inside for a projecting apex formed on the outside of the wall portion.

BRIEF DESCRIPTION OF THE DRAWINGS

Referring now to the drawings, in which the same characters of reference are employed to indicate corresponding similar parts throughout the several figures of the drawings.

DESCRIPTION OF THE PREFERRED EMBODIMENT

Figure 1:
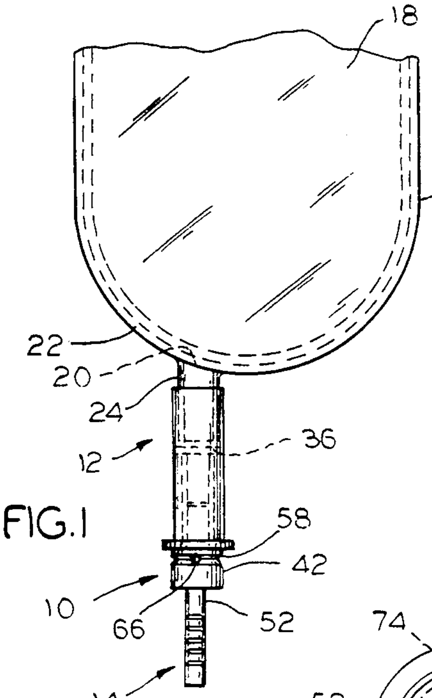
FIG. 1 illustrates the quick release tamper evident closure device operatively sealed to a fluid bag, and embodying the principles of the invention.
Figure 2:
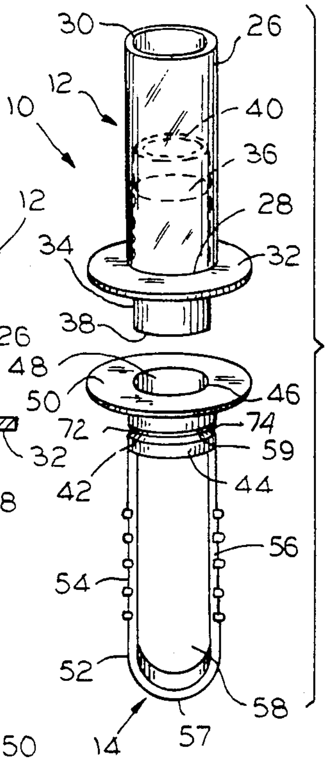
FIG. 2 illustrates in perspective the outlet port section and the closure cap section spaced apart.
Figure 3:
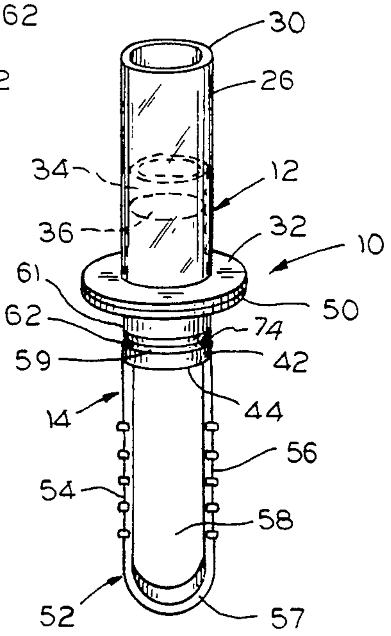
FIG. 3 illustrates in perspective the outlet port section sealed to the closure cap section.
Figure 8:
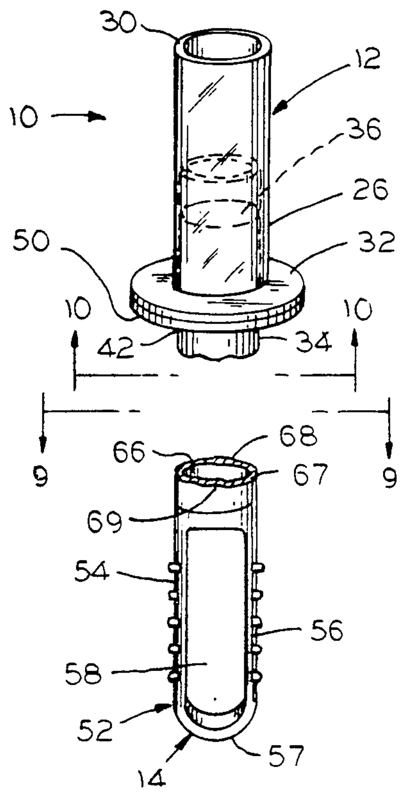
FIG. 8 illustrates the closure cap section severed and spaced from the outlet port section.

Referring now to FIGS. 1, 2 and 3 of the drawing, the reference numeral 10 indicates generally a quick release tamper evident closure device. The quick release closure device 10 includes an outlet port section 12 and a closure cap section 14 (FIG. 2). The outlet port section 12 and the closure cap section 14 are heat sealed or otherwise permanently sealed together as shown in FIG. 3.

The quick release closure device 10 is suitable for providing an easily releaseable and tamper evident outlet closure for a conventional flexible and disposable fluid bag or container 16. These bags are generally used for storing a fluid 18 such as blood or a saline solution or other fluids necessary for the treatment of the patient or needed during surgery. The bag 16 may be constructed from a heat sealable synthetic plastic material such as a polyvinyl chloride or other suitable plastic.

Referring now more particularly to FIG. 1, the bag 16 includes an opening 20 formed in the bottom end 22 thereof. A hollow and open ended projection 24 is sealed or integrally formed to the bag 12 and circumscribes the opening 20 and extends outward (or downward) therefrom to provide a fluid outlet for the bag 16.

The outlet port section 12 (FIGS. 2 and 7) includes an open ended outer tube 26 having an outer end 28 and an inner end 30. A circular collar 32 is sealed to the outside of the outer end 28 of the tube 26.

Figure 7:
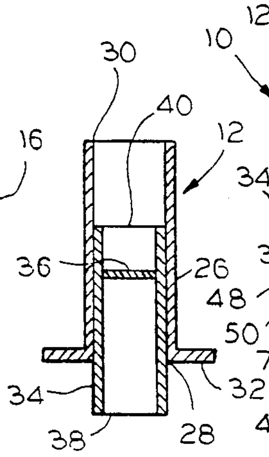
FIG. 7 is a sectional elevational view of the outlet port section of the closure device.

An open ended inner tubular member 34 fits inside the outer tube 26 (FIGS. 2 and 7). The tubular member 34 includes a closure disc 36 positioned between its forward end 38 and rear end 40. The tubular member 34 is positioned inside the outer tube 26. The forward end 38 of the inner tubular member 34 extends further outward than the outer end 28 of tube 26. The rear end 40 of the tubular member 34 is spaced from the inner end 30 of the tube 26. The outlet projection 24 extends inside the outer tube 26

Figure 4:
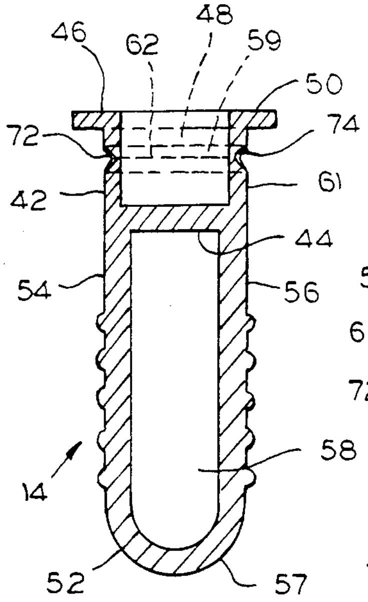
FIG. 4 is a sectional view of the closure cap section, taken on the plane of the line 4—4 in FIG. 5, and viewed in the direction indicated.
Figure 5:
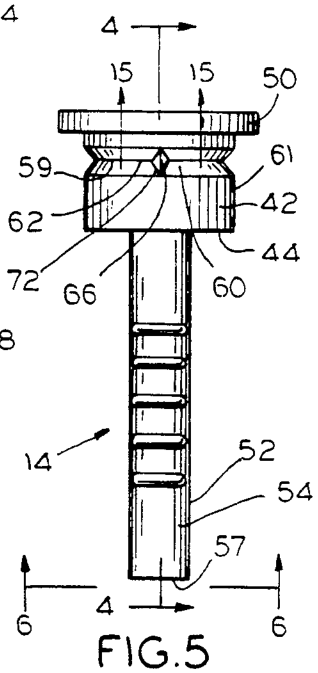
FIG. 5 is a side elevational view of the closure cap section.

The closure cap section 14 (FIGS. 2, 4 and 5) includes a neck portion 42 having a flat front end 44 and an open back end 46 leading into an annular cavity 48. The forward end 38 of the tubular member 34 is received inside cavity 48. A circular shoulder 50 extends around the back end 46 of the neck 42.

A substantially "U" shaped handle 52 is integrally formed to the front end 44 of the neck 42. The handle 52 includes a pair of opposed side bars 54,56 and an arcuate segment 57 linking the side bars together. The side bars 54, 56, the arcuate segment 57 and the front end 44 of the neck 42 define a channel opening 58. The handle 52 is flexible so that the side bars 54,56 and the link segment 57 can be easily spread further apart to receive the finger of the nurse or medical attendant opening the quick release closure device 10. The resiliency of the side bars 54,56 and segment 57 enable the handle 52 to be supported on the finger after the cap section 14 has been severed from the outlet port section 12.

A groove 59 circumscribes the outside of the neck 42. The defining wall 60 of the groove is part of the side wall 61 of the neck 42 defining the cavity 48. The groove 59 provides a continuous tear path 62 for opening the quick release closure device 10. The tear path 62 has substantially less thickness than any other part of the neck 42. The tear path 62 also circumscribes the cavity 48 on the inside of the neck 42.

Figure 6:
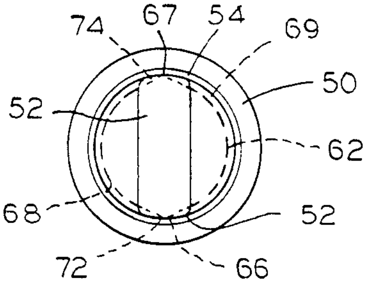
FIG. 6 is a bottom view of the closure cap section in FIG. 5, taken on the plane of the line 6—6 in FIG. 5, and viewed in the direction indicated.
Figure 9:
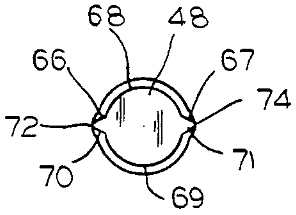
FIG. 9 is a top view of the severed closure cap section, taken on the plane of the line 9—9 in FIG. 8, and viewed in the direction indicated.
Figure 10:
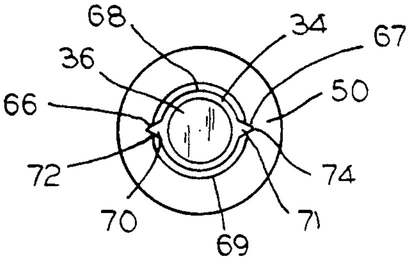
FIG. 10 is a bottom view of the outlet port section after being severed from the closure cap section, viewed as indicated on the plane of the line 10—10 in FIG. 8.

Turning now to FIGS. 6,9 and 10, it will be seen that the tear path 62 includes an apex 66 on one side and an apex 67 at the opposite side. Arcuate portions 68,69 of the tear path 62 are opposed to each other and link with the apexes 66,67. The arcuate portions 68,69 are formed from a radius of a circle, which would be substantially the radius of a horizontal cross section of the cavity 48. The apexes 66,67 protrude outward in comparison with arcuate portions 68,69 of the tear path 62.

A triangular depression 70 is formed in the sidewall 61 on the inside of the neck 42 in communication with the cavity 48 to form a hollow inside for the apex 66 in the tear path 62. A similar triangular depression 71 oppositely formed in the sidewall 61 on the inside of the neck 42, also in communication with the cavity 48, forms a hollow inside for the apex 67.

Thus, the tear path 62 is continuous and includes the projecting apex 66, the arcuate portion 68, the projecting apex 67 spaced from and opposed to the apex 66, and the arcuate portion 69 spaced from and opposed to the arcuate portion 68. The apexes 66 and 67 have the same configuration and the arcuate portions 68 and 69 also have the same configuration. With the triangular depressions 70,71, forming the inside of the apexes 66,67 the wall thickness throughout the tear path 62 is substantially the same eventhough the projecting apexes 66,67 are included in the tear path.

The outside of the apex 66 is part of a substantially diamond shaped bulge 72 protruding inside the groove 59, and the outside of the apex 68 is also part of a substantially diamond shaped bulge 74. Hence, the apexes 66,67 protrude outward inside the groove 59 as compared to the arcuate portions 68,69.

Figure 11:
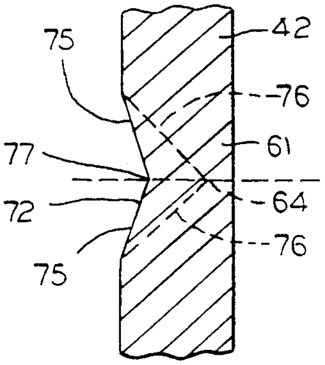
FIG. 11 is an enlarged side sectional view of the bulge in the groove formed in the neck of the closure cap section to provide an apex, and showing the adjacent deeper portion of the groove in phantom.

As may be seen from FIG. 11, which illustrates the bulge 72 (would be the same for bulge 74), the incline 75 for the bulge 72 in the groove 59 is subtantially less than for the incline 76 at the other parts of the groove 59. It has been found that an angle of approximately 74 degrees for the bulge incline 75 and an angle of approximately 47 degrees for the other parts of the groove 59 are suitable. The apex 66 of the tear path 62 would be at the center vertex 77 for the intersecting inclines 75 of the bump 72. The center vertex 78 for the intersecting inclines 76 would also be on the tear path 62 for the arcuate portions 68,69.

Thus, the groove 59 at the bulges 72,74 has less depth into the outside of the side wall 61 of the neck 42 than the remaining portions of the groove 59. Hence, the arcuate portions 68, 69 extend deepest inside the groove 59 and the apexes 66,67 project outward.

The side bar 54 of the handle 52 is aligned with the apex 6, and similarly the side bar 56 is aligned with the apex 67. The handle 52 lies on a plane substantially perpendicular with the tear path 62 (FIG. 6). Thus, the initial pulling or tearing force applied to the handle 52 is focused at the apexes 66,67 of the tear path 62.

When assembling the quick release tamper evident closure device 10 (FIGS. 2 and 3), the forward end 38 of the inner tubular member 34 is received in the cavity 48 in the neck portion 42. The collar 32 and the shoulder 50 abutt each other and are sealed together. Any tampering of the closure device 10 would be immediately evident upon a visual inspection of the device.

To open the quick release tamper evident closure 10, a finger is positioned inside the opening 58 of the handle 52. If the finger is larger than the opening 58 the flexible bars 54,56 and segment 57 of the handle 52 are spread apart to accommodate the finger in the opening 58. Force is then applied to the handle in the forward or outward direction.

The force is focused initially at the apexes 66,67 and the thin wall at the apexes rip open and thereafter the thin wall along the arcuate portions 68,69 of the the tear path 62 rips until the closure cap section 14 is totally severed from the outlet port section 12. Now the outlet port section 14 may be opened for removing the contents from the bag 12. A spike may be used to pierce through the disc 36 and connect an IV attachment or other attaching means for draining the contents out of the bag 12.

Figure 12:
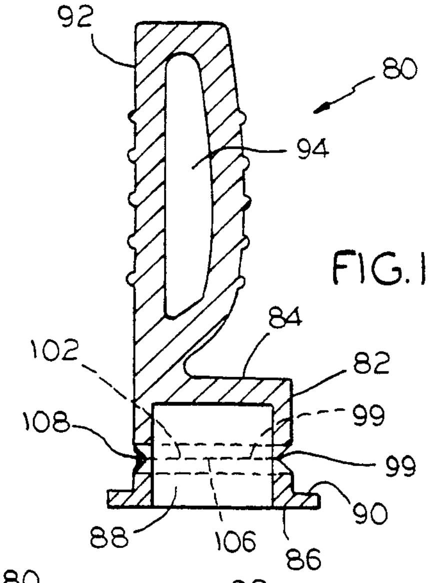
FIG. 12 is a sectional view of an alternate embodiment for the closure cap section of the quick release closure device, having a single apex in the tear path for opening the closure device.
Figure 13:
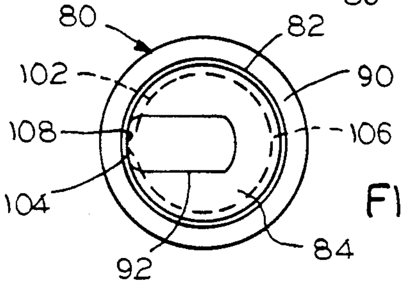
FIG. 13 is a top view of the closure cap section of FIG. 12.

An alternate embodiment for the closure cap section is indicated generally by the reference numeral 80 and illustrated in FIGS. 12 and 13. The closure cap section 80 includes a neck portion 82 having a flat front end 84 and an open back end 86 leading into an annular cavity 88. The forward end 38 of the tubular member 34 is received inside the cavity 88. A circular shoulder 90 extends around the back end 86 of the neck 82.

An elongated handle 92 is integrally formed to the front end 84 of the neck 82. An elongated opening 94 is formed in the handle 92.

A groove 99 circumscibes the outside of the neck 82. The defining wall of the groove 99 is part of the side wall of the neck 82 defining the cavity 88. The deepest part of the groove 99 around the outside of the neck 82 including at the apex 104 of the projection 108, provides a continuous tear path 102 for opening the quick release closure device 10. The tear path 102 has substantially less thickness than any other part of the neck.

As may be seen from FIG. 13, the tear path 102 includes an apex 104 having a triangular shape. The remaining portion 106 of the tear line is arcuate and formed from a radius of a circle which would be substantially the radius of the cavity 88 taken from a horizontal plane as viewed in FIG. 12.

The apex 104 is part of a projecting bulge 108 in the groove 99. The groove 99 inclines substantially less at the bulge 108 than at any other location in the groove 99. The depth of the groove is the least at the bulge 108.

The handle 92 is aligned with the apex 104. When opening the quick release closure device 80 having the closure cap 80, the handle 92 is pulled outward to start the tearing of the tear path 102 at the apex 104 and the tearing continues along the arcuate portions 106 of the tear path 102, to fully sever the closure cap 80 from the outlet port section 12, to thereby access the tubular member 34 of the outlet port section 12.

Figure 14:
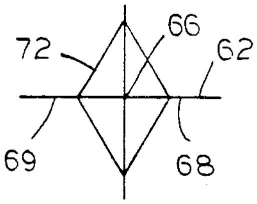
FIG. 14 is an enlarged side view of the apex projection in the tear path on the outside of the closure cap, as shown in FIG. 5.
Figure 15:
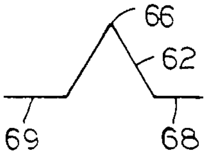
FIG. 15 is a horizontal sectional view of the apex projection in the tear path, taken on the plane of the line 15—15 in FIG. 5 and viewed in the direction indicated, to show the outward projecting incline of the apex as compared with the adjacent arcuate portions of the tear path.

Turning now to FIGS. 14 and 15, it will be seen that the tear path is inclined upward (outward in FIG. 5) from the arcuate portion 69 to the apex 66 and inclines downward (inward in FIG. 5) until reaching the arcuate portion 68, in a substantially triangular configuration. The inclining and declining of the tear path would be the same at the apex 67. Thus, the tear path 62 is continuous and includes projection portions 72,74 having the apexes 66,67.

There are various modifications of the invention of a quick release tamper evident closure device for use with fluid bags, the scope of which is limited solely and defined by the appended claims.

I claim:

1. A quick release tamper evident closure device for fuse with fluid bags having a fluid discharge opening and comprises:

a port section including a tubular means for attaching to the fluid bag to communicate with the fluid discharge opening;

a cap section for securing to the port section to close said port section, said cap section including a neck portion having a front end and a back end and a side wall between the ends, said back end of the neck having an opening leading into a cavity formed inside the neck portion, said tubular means extending inside said cavity;

an annular tear path formed in said neck portion for severing said neck portion to access said tubular means; and a handle secured to the front end of the neck portion, said handle including an enclosed opening, said handle being flexible for accommodating a finger inside said opening, the application of an outward pulling force with said finger causing said severing of said tear path.

2. The closure device of claim 1, wherein:

said handle has a substantially "U" shape having spaced apart inner ends secured to the front end of the neck portion, the inside surface of said handle and said front end of the neck portion defining said enclosed handle opening.

3. The closure device of claim 1, wherein said cap section further includes:

an annular groove formed in the side wall of the neck portion, said groove including an arcuate portion recessed to an inner surface: and a bump recessed in said groove and formed to said inner surface and extending outward from said inner surface, said inner surface being recessed further inward in said sidewall than said bump, said tear path including said bump and said inner surface, said bump being the beginning point for ripping said tear path upon the application of said pulling force.

4. A closure device of claim 3, wherein said handle is positioned substantially aligned with said bump.

5. The closure device of claim 4, wherein: the wall defining said tear path is substantially thinner than adjacent portions of the sidewall of the neck portion.

6. A quick release tamper evident closure device for use with fluid bags having a fluid discharge opening, and comprising:

a port section for attaching to the fluid bag to communicate with the fluid discharge opening:

a cap section for securing to the port section to close said port section, said cap section including a neck portion having a front end and a back end, said back end being associated with the port section;

a groove formed in the neck portion between the front and back ends and recessed to an inner surface, the inner surface of said groove having a first end and a second end;

a first apex portion having an outer vertex, said first apex formed to and extending outward from the first end of the inner surface;

a second apex portion having an outer vertex, said second apex formed to and extending outward from the second end of the inner surface, said first apex being opposed to the second apex, the inner surface of the groove and said first apex and said second apex providing a tear path for severing said neck portion to access said port section: and a handle extending outward from the neck portion, the application of an external force to said handle causing ripping of said tear path.

7. The closure device of claim 6, wherein: said handle includes:

a pair of spaced apart bars, each of said bars having an inner end and an outer end; and a rod linking the outer ends of said bars together, the inner ends of each of said bars being attached to the front end of said neck portion, (said opening of the handle being defined by said bars and said rod and said neck) said bars and said rod and the front end of said neck portion defining an opening, each of said bars being aligned with one of said apex portions, said bars and said rod being movable outward for accommodating a finger inside said opening.

8. The closure device of claim 3, wherein:

the neck portion includes a cavity, said tubular means being received in said cavity, the defining wall of said cavity including the portion of the wall defining said tear path and further includes:

a depression formed in the side wall of the neck portion in communication with the cavity to provide a hollow inside for said apex projection.

9. The closure device of claim 8, wherein said depression is formed into a substantially triangular apex configuration.

10. The closure device of claim 3, wherein said groove encircles the neck between the front end and the back end.

11. The closure device of claim 6, wherein said groove encircles the neck between the front end and back end, the depth in the groove is less at the apex projections than at the other locations in the groove.

12. The closure device of claim 6, wherein said groove includes a pair of spaced apart angled walls defining said groove, said angled walls of the groove incline inward and converge together at said inner surface.

13. A quick release tamper evident closure device for use with a bag containing fluid comprising:

an outlet port section including tubular means for discharging fluid from said bag;

a closure cap section secured to the outlet port section for closing access to the tubular means, said closure cap including a neck portion having a front end, a back end and a side wall connecting the front and back ends together;

said back end of the neck portion being open and leading into a cavity formed inside the neck portion, said tubular means extending inside said cavity; and a substantially annular groove formed on the outside of the neck portion to define a tear path for severing the side wall of the neck portion to access the tubular means inside the cavity, said tear path including a pair of opposed curved portions and a pair of opposed apex portions, said curved portions merging with said apex portions.

14. The closure device of claim 13 includes:

a handle formed on the front end of the neck portion, said handle being aligned with at least one of the apex portions.

15. The closure device of claim 12, wherein each of said apexes is a projection in said groove as compared with said curved portions.

16. The closure device of claim 13, wherein said cured portions are substantially equal arcuate portions.

17. A quick release tamper evident closure device for use with a fluid bag having a fluid discharge opening, and comprising:

a port section including tubular means for attaching to the fluid bag to communicate with the fluid discharge opening;

a cap section for securing to the port section to close said port section, said cap section including a neck portion having a front end and a back end, said back end of the neck having an opening leading into a cavity formed inside the neck portion, said cavity being defined by an inside wall surface, said tubular means extending inside said cavity;

a pair of opposed arcuate grooves formed in the outside of the neck portion and each groove recessed to an inner surface, the inner surface of each groove including a first end spaced from a second end;

a first apex portion having an outer vertex, said first apex merging with the first end of each of said inner surfaces of said grooves; and a second apex portion having an outer vertex, said second apex merging with the second end of each of said inner surfaces of said grooves, the inner surfaces of said grooves and said first apex and said second apex defining a tear path for severing said neck portion to access said cavity and said tubular means.

18. The closure device of claim 12 includes:

a substantially "U" shaped handle having spaced apart inner ends secured to the front end of the neck portion, the handle and the front end of the neck portion defining an enclosed handle opening, each of said inner ends of the handle aligned with one of the apexes so that the application of a pulling force is initially focused at said apexes for severing the tear path, said handle being flexible for accommodating a finger inside said handle opening.

19. The closure device of claim 15, wherein the part of said tear path at said apex includes an outward inclining segment and an inward inclining segment meeting at a vertex to provide a substantially triangular configuration.

20. The closure device of claim 17, wherein each of said apex portions includes:

an outward inclining segment having an inner end and an outer end; and an inward inclining segment having an inner end and an outer end, the inner end of said outward inclining segment being connected to said first end of the inner surface of one of said grooves, the inner end of said inner inclining segment being connected to said first end of the inner surface of the other said groove, said outer ends of said segments being attached together at said vertex of the corresponding apex, so that said segments form a substantially triangular configuration along said tear path.

21. The closure device of claim 17, wherein:

said first apex portion and said second apex portion are recessed inward from the outside of the neck portion, said inner surfaces of said arcuate grooves being recessed further inward than said first and second apex portions.

22. The closure device of claim 21 includes:

a first depression forming a hollow inside for said first apex portion; and a second depression forming a hollow inside for said second apex portion, said depressions being formed outward from said inside wall surface of the neck portion an din communication with said cavity, the defining surface for each of said depressions having a substantially triangular configuration after being intersected by a plane passing through said tear path.

23. The closure device of claim 17, wherein each of said apexes form a substantially diamond configuration.

24. The closure device of claim 17, wherein said tear path is a continuous annular path circumscribing the neck portion of the cap section.

25. The closure device of claim 17, wherein each of said apexes is recessed inward in the neck of the cap at substantially an angle of 74 degrees and each of said grooves incline inward to said inner surface at substantially an angle of approximately 47 degrees.

26. A quick release tamper evident closure device for use with fluid bags having a fluid discharge opening, and comprising:

a port section for attaching to the fluid bag to communicate with the fluid discharge opening;

a cap section for securing to the port section to close said port section, said cap section including a neck portion having a front end and a back end, said back end being associated with said port section;

a substantially annular tear path is formed in the neck portion, said tear path including an arcuate inner surface recessed inward from the outside of said neck portion and a bump portion formed to said inner surface and projecting outward therefrom said inner surface being recessed inward further than said bump; and a handle extending outward from the neck portion, the application of an external force to said handle causing ripping of said tear path for accessing said port section.

27. The closure device of claim 26, wherein said bump has a substantially apex shape having an outer vertex, said bump having a substantially triangular configuration after said tear path is severed.

28. The closure device of claim 27 wherein said neck portion includes a cavity defined by an inside surface and further includes:

a depression formed inside said apex, said depression being formed outward from said inside surface and in communication with said cavity, said depression having a substantially triangular configuration after being intersected by a plane passing through said tear path.

* * * * *